(12) United States Patent
Wieters et al.

(10) Patent No.: US 11,596,295 B2
(45) Date of Patent: Mar. 7, 2023

(54) VIDEO ENDOSCOPE

(71) Applicant: OLYMPUS WINTER & IBE GMBH, Hamburg (DE)

(72) Inventors: Martin Wieters, Barsbuettel (DE); Annika Goehring, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 12 days.

(21) Appl. No.: 17/402,934

(22) Filed: Aug. 16, 2021

(65) Prior Publication Data
US 2022/0053997 A1 Feb. 24, 2022

(30) Foreign Application Priority Data
Aug. 19, 2020 (DE) .......................... 102020121755.2

(51) Int. Cl.
*A61B 1/00* (2006.01)
*A61B 1/05* (2006.01)
*A61B 1/12* (2006.01)

(52) U.S. Cl.
CPC ............ *A61B 1/00114* (2013.01); *A61B 1/05* (2013.01); *A61B 1/128* (2013.01); *A61B 2562/166* (2013.01)

(58) Field of Classification Search
CPC ....... A61B 1/00114; A61B 1/05; A61B 1/128; A61B 2562/166; A61B 1/00018; A61B 1/00071; A61B 1/051; A61B 1/0011; A61B 1/00096; A61B 1/0684; A61B 1/015; A61B 1/267; A61B 1/053; A61B 8/4416; A61B 8/12; A61B 1/0051; A61B 1/00082; A61B 1/018; H05B 3/34; H05B 2203/003; H05B 3/42; G02B 23/2423; G02B 23/2484;
(Continued)

(56) References Cited

U.S. PATENT DOCUMENTS 5,941,817 A * 8/1999 Crawford ........... A61B 1/00071 600/110
6,468,221 B2 10/2002 Ohara et al.
(Continued)

FOREIGN PATENT DOCUMENTS

DE 10122710 A1 11/2001
DE 10157026 A1 9/2002
(Continued)

OTHER PUBLICATIONS

German Office Action dated Jan. 11, 2021 issued in DE 102020121755. 2.

*Primary Examiner* — Anh Tuan T Nguyen
*Assistant Examiner* — Sung Ham
(74) *Attorney, Agent, or Firm* — Scully, Scott, Murphy & Presser, P.C.

(57) ABSTRACT

A video endoscope including: an elongated shaft having an inner shaft tube and an outer shaft tube; and an electrical connecting element extending in a longitudinal direction of the shaft between the inner shaft tube and the outer shaft tube. Wherein the electrical connecting element is configured as a flexible printed circuit board with at least one conducting path which is routed substantially parallel to a longitudinal axis of the shaft, and the electrical connecting element is routed at an angle with respect to the longitudinal axis of the shaft at at least one location of the shaft.

11 Claims, 4 Drawing Sheets

(58) Field of Classification Search
CPC ......... H04N 2005/2255; H04N 5/2254; H04N 5/2253; H05K 1/118
See application file for complete search history.

(56) References Cited

U.S. PATENT DOCUMENTS

| | | |
|---|---|---|
| 2001/0041839 A1 | 11/2001 | Ohara et al. |
| 2010/0016671 A1 | 1/2010 | Wieters et al. |
| 2012/0310043 A1 | 12/2012 | Hu et al. |
| 2014/0221743 A1* | 8/2014 | Sugiyama .......... A61B 1/00097 600/109 |
| 2014/0371530 A1* | 12/2014 | Wieters .............. G02B 23/2476 600/109 |
| 2017/0007110 A1* | 1/2017 | Ide .......................... A61B 1/05 |
| 2021/0059745 A1* | 3/2021 | Highsmith ............. A61B 5/287 |
| 2022/0022740 A1* | 1/2022 | Truckai .................... A61B 1/07 |

FOREIGN PATENT DOCUMENTS

| | | |
|---|---|---|
| DE | 102008031924 A1 | 1/2010 |
| DE | 102019100144 A1 | 7/2020 |
| DE | 102019104489 A1 | 8/2020 |

* cited by examiner

VIDEO ENDOSCOPE

CROSS-REFERENCE TO RELATED APPLICATION

The present application is based upon and claims the benefit of priority from DE 10 2020 121 755.2 filed on Aug. 19, 2020, the entire contents of which is incorporated herein by reference.

BACKGROUND

Field

The present disclosure relates to a video endoscope and more particularly to a video endoscope having an elongated shaft comprising an inner shaft tube and an outer shaft tube, and having an electrical connecting element running in the longitudinal direction of the shaft between the inner shaft tube and the outer shaft tube, wherein the electrical connecting element is configured as a flexible printed circuit board having at least one conducting path which extends substantially parallel to a longitudinal axis of the shaft.

Prior Art

Endoscopes have long been used in medicine to examine or treat cavities in the body of a human or animal patient that are difficult to access. For this purpose, endoscopes usually have an elongated shaft with a main body attached to its proximal end, where the endoscope can be held. At the distal end of the shaft, an objective lens is usually disposed, the image of which is transmitted to the proximal end via an optical or electronic image guide and is made available there by suitable means for viewing and/or evaluation. The distal end of the shaft is usually hermetically sealed by a window to prevent the ingress of contaminants or liquids.

The shaft of an endoscope may be flexible or rigid. Rigid shafts are constructed from several shaft tubes disposed one inside the other; they are mainly used in urology, gynaecology and laparoscopy.

In laparoscopy, the endoscope is inserted through an artificial access into a patient's abdominal cavity which is expanded with a gas. Moisture may condense on the window of the endoscope, especially at the beginning of a procedure when the endoscope is at a much lower temperature than the gas in the patient's abdominal cavity. This may sometimes obstruct the view of the attending physician to such an extent that he must interrupt the procedure and clean the window.

To avoid such condensation, endoscopes comprising a heating device for the window have been known for some time. By means of the heating device, the window of the endoscope is heated to an elevated temperature even before it is inserted into the patient's abdominal cavity, so that the risk of condensation is significantly reduced.

From DE 10 2008 031 924 A1, for example, an endoscope is known in which a heating foil is disposed between an outer shaft tube and an inner shaft tube. Patent application DE 10 2019 104 489.8 discloses an endoscope with a heating foil, which has an extension in the form of a flexible printed circuit board for contacting at the proximal end of the shaft.

Contacting the heating foil by means of a flexible printed circuit board requires significantly less axial installation space compared with contacting via ordinary cables and the contact is less complicated to introduce during assembly of an endoscope.

However, contacting via a flexible printed circuit board does not allow the cable length to be adapted to any tolerances in the length and position of components of the shaft or the heating foil. Due to the structure of the flexible printed circuit board, the distance between a distal section of the heating foil and proximal contacting points of the flexible printed circuit board is precisely specified. Since the installation of the flexible printed circuit board in an annular space between an inner and an outer shaft tube does not allow any wrinkling or looping of the flexible printed circuit board, any length or positional tolerance may cause a displacement of the proximal contacting points of the printed circuit board with respect to contact elements to be connected thereto, which makes a connection more difficult or, in the worst case, impossible.

SUMMARY

It is therefore an object to provide a video endoscope which is improved with respect to the described problem.

Such object can be achieved by a video endoscope having an elongated shaft, comprising an inner shaft tube and an outer shaft tube and having an electrical connecting element extending in the longitudinal direction of the shaft between the inner shaft tube and the outer shaft tube, wherein the electrical connecting element is configured as a flexible printed circuit board with at least one conducting path, which is routed substantially parallel to a longitudinal axis of the shaft, which is further configured in that the electrical connecting element is routed at an angle with respect to the longitudinal axis of the shaft at at least one location of the shaft.

By appropriately routing the circuit board, the location of proximal contact points of the flexible circuit board can be adjusted by slightly shifting the routing of the circuit board.

In an embodiment of a video endoscope, the electrical connecting element may comprise a distal section, a proximal section, and a transition section, wherein the electrical connecting element is routed parallel to the longitudinal axis of the shaft at the distal section and at the proximal section, and is routed at least partially at an angle with respect to the longitudinal axis of the shaft at the transition section. In this case, the connecting element has a basically "Z"-shaped routing, with the transition section allowing axial displacement of the proximal and distal sections relative to each other.

In another embodiment of a video endoscope, an annular space between the inner and outer shaft tubes may be widened in the region of the transition section of the connecting element. In this expanded region of the annular space, the transition section of the connecting element may vary in its routing to compensate for length tolerances.

In another embodiment of a video endoscope, a diameter of the inner shaft tube and the outer shaft tube may change along the shaft at at least one location, wherein the diameter change of the inner shaft tube is offset relative to the diameter change of the outer shaft tube in the longitudinal direction of the shaft so that the annular space between the inner and the outer shaft tube is widened in the region of the diameter changes.

The shaft tubes of video endoscopes often exhibit step-like diameter changes in the proximal section, with the diameter expanding in the proximal direction of the shaft. These diameter changes are usually intended to facilitate the mounting of components located in the shaft. In the area of such diameter changes, an expansion of the annular space may be achieved particularly easily by means of the axial offset.

A guiding element for the connecting element may be disposed in the region of the expanded annular space. The guiding element may serve to protect the connecting element from damage during assembly of the video endoscope.

In this regard, the guiding element may comprise an annular sleeve which passes over the inner shaft tube and the connecting element. The sleeve may comprise an internal groove which guides the connecting element laterally.

In another embodiment of a video endoscope, the guiding element may be made of or comprise an electrically insulating material. This may effectively insulate the connecting element from the outer shaft tube in the transition section.

The connecting element may be fixed to the inner shaft tube in the region of the proximal and/or the distal section. The connecting element may be fixed to the inner shaft tube by one or more electrically insulating heat-shrink tubings. Such heat-shrink tubings can also serve to electrically insulate the connecting element from the outer shaft tube.

The guiding element may overlap a first heat-shrink tubing which fixes the distal portion of the connecting element, and a second heat-shrink tubing which fixes the proximal portion of the connecting element may overlap the guiding element.

The connecting element may comprise control and/or supply lines of a heating device for a distal window of the endoscope.

BRIEF DESCRIPTION OF THE DRAWINGS

The embodiments will be explained in more detail below with reference to some exemplary embodiments. In this context, the embodiments shown in the figures are merely intended to contribute to a better understanding of the invention without limiting the scope of the claims, in which:

DETAILED DESCRIPTION

Figure 1:
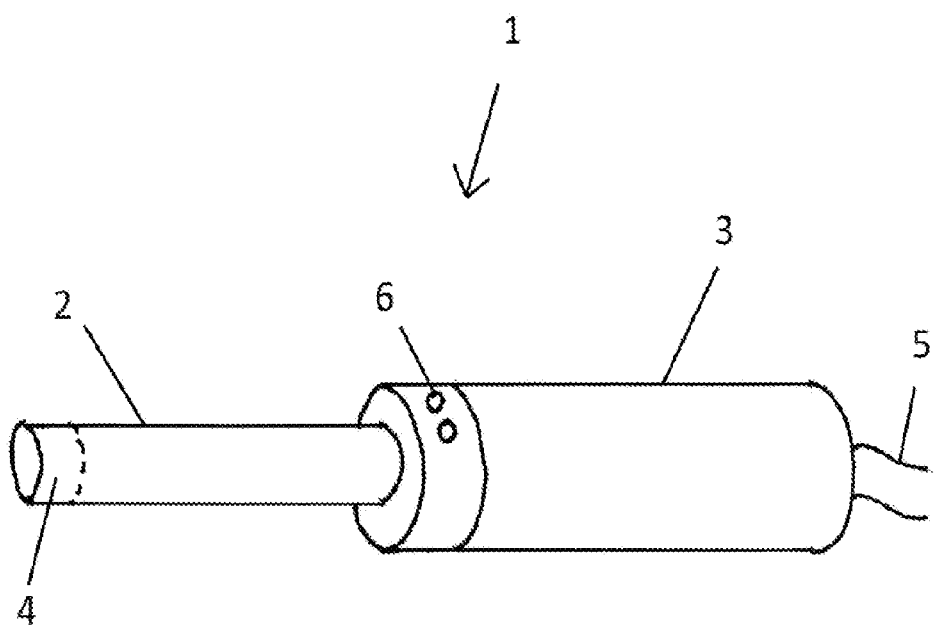
FIG. 1 illustrates a video endoscope.

FIG. 1 shows an endoscope 1 with an elongated shaft 2 and a main body 3.

An objective lens 4 is disposed in the distal end of the shaft 2. The image from the objective lens is converted into electrical video signals by an electronic image converter (an image sensor), not shown, and transmitted to the main body 3. From the main body 3, the video signals are output via a cable 5, if necessary after electronic pre-processing.

Control switches 6 are provided in the distal area of the main body, via which functions of the endoscope 1 or connected devices may be controlled. Signals from the control switches 6 are also routed via the cable 5.

Figure 2:
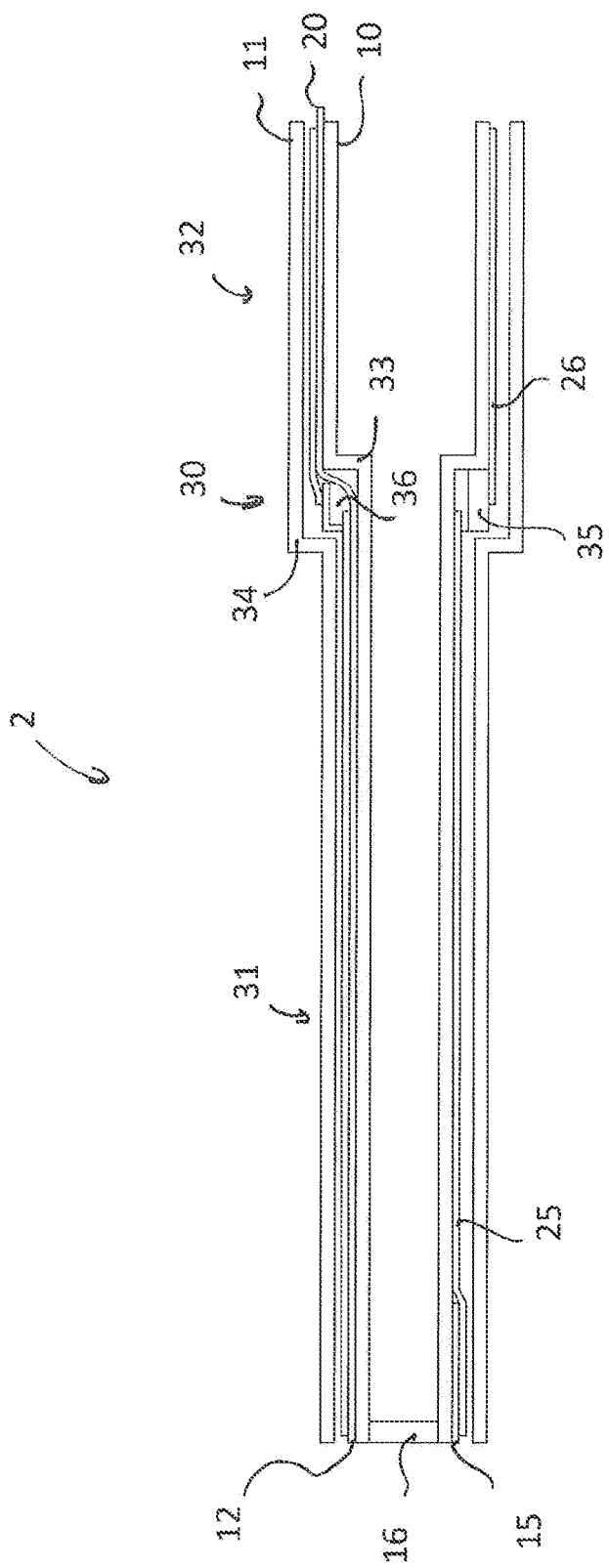
FIG. 2 illustrates the shaft of a video endoscope in a sectional view.

FIG. 2 shows the shaft 2 of the endoscope 1 in a principal sectional view, wherein components of the endoscope which are not essential for the understanding of the embodiments are not shown for a better overview.

The shaft 2 comprises an inner shaft tube 10 as well as an outer shaft tube 11. In an annular space between the inner shaft tube 10 and the outer shaft tube 11 an electrical connecting element 12 is disposed, which is a flexible printed circuit board with conducting paths (not shown).

In the example shown, the connecting element 12 comprises control and/or supply lines of a heating device 15 for a window 16 which distally closes off the inner shaft tube 10. The heating device 15 is configured as a heating foil which is placed around the distal end of the inner shaft tube 10. In this example, the heating foil is made in one piece with the connecting element 12.

At the proximal end, the connecting element 12 comprises a contacting area 20. The contacting area 20 provides solder pads, which are not shown, for connecting the connecting element to a supply circuit of the heating device 15, which is also not shown.

For securing the connecting element 12 to the inner shaft tube 10, and for electrically insulating the connecting element 12 from the outer shaft tube 11, the connecting element 12 and the inner shaft tube 10 are encased in a heat-shrink tubing 25 in the distal region and in a heat-shrink tubing 26 in the proximal region. The heat-shrink tubings 25, 26 are made of electrically insulating material.

Both the positioning of the heating device 15 on the inner shaft tube 10 and the length of the shaft tubes 10, 11 and the connecting element 12 are subject to manufacturing tolerances. In order to nevertheless enable precise positioning of the connection area 20 and thus straightforward contacting, the connection element 12 is routed at an angle with respect to a longitudinal axis of the shaft 2 in a transition section 30, which is provided between a distal section 31 and a proximal section 32 of the connection element 12. By slightly adjusting the routing of the connecting element 12 in the transition section 30, length and position tolerances of the system can be compensated for.

To provide sufficient space for different configurations of the connecting element 12, the annular space between the inner shaft tube 10 and the outer shaft tube 11 is widened in the area of the transition section 30. For this purpose, diameter changes 33, 34 of the inner shaft tube 10 and the outer shaft tube 11 are axially offset from each other.

To prevent damage to the connecting element 12 during assembly of the shaft 2, a guiding element for the connecting element 12 is provided in the region of the transition section 30. The guiding element comprises an annular sleeve 35, which is slid over the inner shaft tube 10 and the connecting element 12. The sleeve 35 comprises an internal groove 36, which guides the connecting element 12 laterally. The sleeve 35 is made of electrically insulating material, for example PEEK.

The sleeve 35 engages over the heat-shrink tubing 25. At the same time, the heat-shrink tubing 26 engages over the sleeve 35. As a result, the connecting element 12 is electrically insulated along its entire length with respect to the outer shaft tube 11.

Figure 3A:
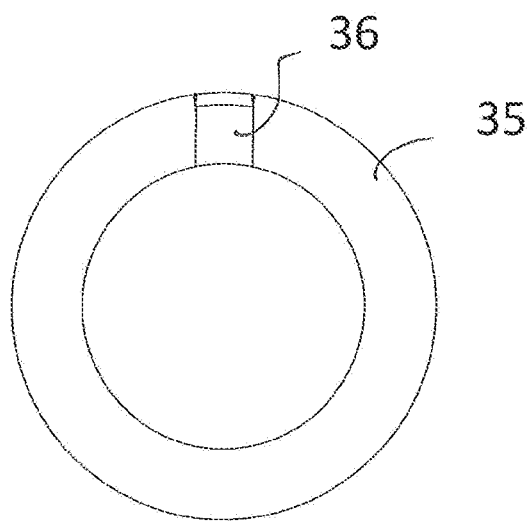
FIGS. 3a, 3b illustrate a sleeve.
Figure 3B:
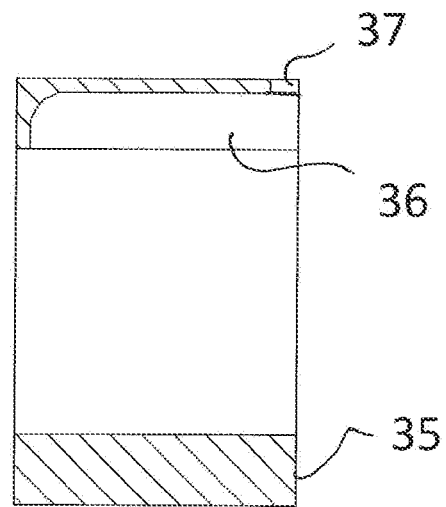

The sleeve 35 is shown in more detail in FIGS. 3a, 3b. The inner groove 36 is configured to be slightly wider than the connecting element not shown in FIGS. 3a, 3b, so that the latter is guided laterally in the groove 36. The connecting element may assume different shapes in the groove 36 so that positional and length tolerances of the individual components may be compensated.

A recess 37 is provided at the distal end of the groove 36, through which the connecting element 12 may be guided outward.

In FIGS. 3a, 3b, the sleeve 35 is shown with a cylindrical cross-section. Deviating therefrom, the sleeve 35 may also be completely or sectionally conical.

Figure 4:
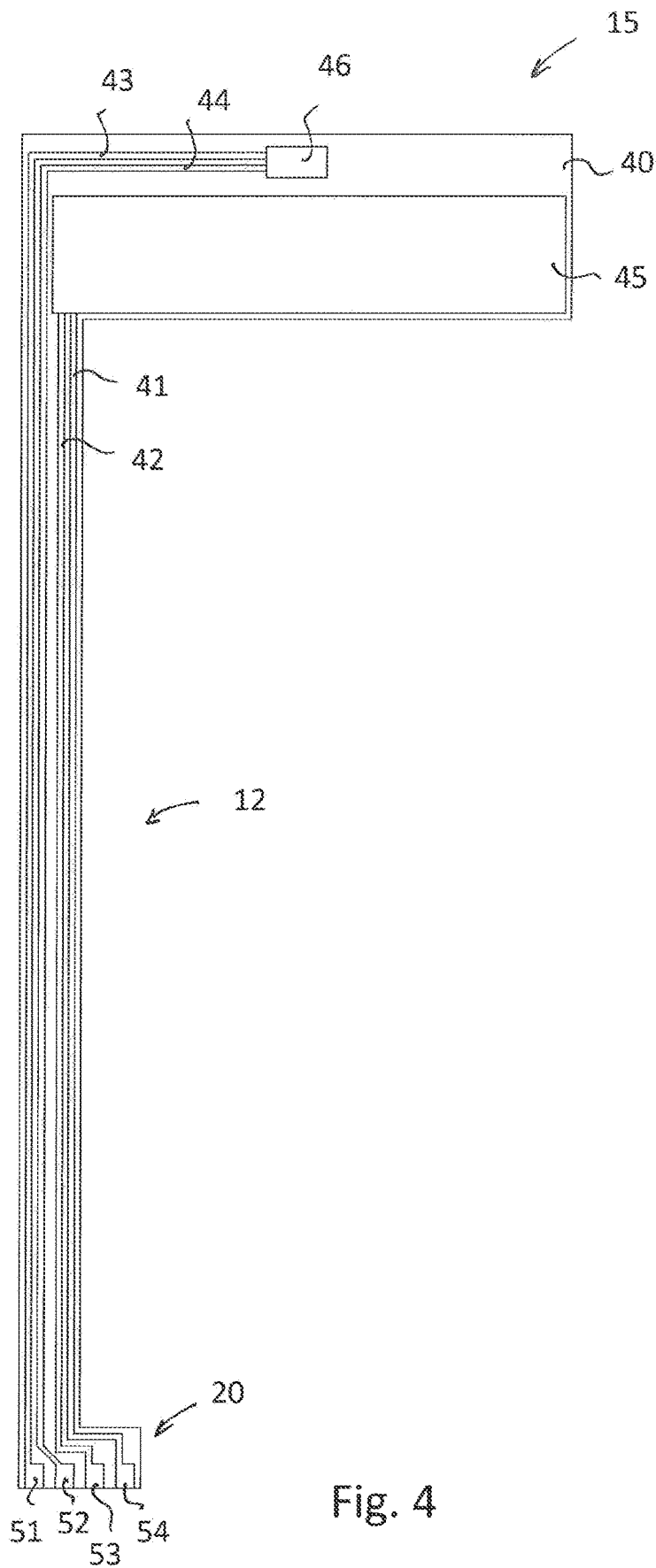
FIG. 4 illustrates a heating device with connecting element.

FIG. 4 shows the heating device 15 with the connecting element 12 in an unfolded state. The heating device 15 and the connecting element 12 consist of a one-piece foil 40 of a carrier material, for example polyimide, to which conducting paths 41, 42, 43, 44 are applied.

In the region of the heating element 15, the conducting paths 41, 42 are connected to a heating resistor 45. The structure of the heating resistor 45 is not shown; it may be configured, for example, as a meandering conducting path. The conducting paths 43, 44 are connected to a temperature sensor 46, which is required for controlling the heating device. The temperature sensor 46 may comprise one or more thermistors. In the case of several thermistors, these may be connected in a bridge circuit; for this purpose, more than two conducting paths may be provided for the temperature sensor.

In the proximal area, the connecting element 12 opens into the connection area 20, where the conducting paths 41, 42, 43, 44 end in solder pads 51, 52, 53, 54, which may be connected to a control circuit not shown.

The endoscope described above is only one possible embodiment of the invention, other embodiments are also possible. For example, an endoscope shaft may have more than two shaft tubes which are arranged one inside the other. In this case, the shaft tubes between which the connecting element is located are to be understood as the inner or outer shaft tube in the sense of the invention, even if additional outer or inner shaft tubes are present.

Instead of the inner shaft tube, another shaft tube, for example the outer shaft tube, may also be closed by a window.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A video endoscope comprising:
    an elongated shaft having an inner shaft tube and an outer shaft tube; and
    an electrical connecting element extending in a longitudinal direction of the shaft between the inner shaft tube and the outer shaft tube;
    wherein the electrical connecting element is configured as a flexible printed circuit board with at least one conducting path which is routed substantially parallel to a longitudinal axis of the shaft, and
    the electrical connecting element is routed at an angle with respect to the longitudinal axis of the shaft at at least one location of the shaft;
    wherein the electrical connecting element comprises a distal section, a proximal section, and a transition section disposed between the distal section and the proximal section, the electrical connecting element being routed parallel to the longitudinal axis of the shaft at the distal section and at the proximal section, and is routed at least partially at the angle with respect to the longitudinal axis of the shaft at the transition section; and
    an annular space between the inner and outer shaft tubes is widened in a region of the shaft corresponding to the transition section of the connecting element as compared to an annular space between the inner and outer shaft tubes in regions corresponding to the distal section and the proximal section of the connecting element.

2. The video endoscope according to claim 1,
    wherein a first diameter of the inner shaft tube and a second diameter of the outer shaft tube change along the shaft at at least one location, wherein the change of the first diameter of the inner shaft tube is offset relative to the change in the second diameter of the outer shaft tube in the longitudinal direction of the shaft such that the annular space between the inner shaft tube and the outer shaft tube in the regions corresponding to the transition section of the connecting element is widened at the at least one location.

3. The video endoscope according to claim 2, further comprising a guide for guiding the connecting element, the guide being disposed at the at least one location.

4. The video endoscope according to claim 3, wherein the guide comprises an annular sleeve which passes over the inner shaft tube and over the connecting element.

5. The video endoscope according to claim 4, wherein the sleeve comprises an internal groove through which the connecting element is angled with respect to the longitudinal axis of the shaft.

6. The video endoscope according to claim 3, wherein the guide is at least partially formed of an electrically insulating material.

7. The video endoscope according to claim 1, wherein the connecting element is fixed to the inner shaft tube in one or more of a proximal end of the connecting element or a distal end of the connecting element.

8. The video endoscope according to claim 7, wherein the connecting element is fixed on the inner shaft tube by one or more electrically insulating heat-shrink tubings.

9. The video endoscope according to claim 8, further comprising a guide for guiding the connecting element, the guide being disposed at the at least one location;
    wherein the one or more heat shrinking tubings comprise a first heat shrink tubing and a second heat shrink tubing;
    the first heat shrink tubing having a distal end which fixes the distal end of the connecting element and the first heat shrink tubing having a proximal end that is overlapped by the guide; and
    the second heat-shrink tubing having a proximal end which fixes the proximal end of the connecting element and the second heat shrink tubing having a distal end that overlaps the guide.

10. The video endoscope according to claim 1, wherein the connecting element comprises one or more of control and supply lines of a heater configured to heat a distal window of the shaft.

11. A video endoscope comprising:
    an elongated shaft having an inner shaft tube and an outer shaft tube; and
    an electrical connecting element extending in a longitudinal direction of the shaft between the inner shaft tube and the outer shaft tube;
    wherein the electrical connecting element is configured as a flexible printed circuit board with at least one conducting path which is routed substantially parallel to a longitudinal axis of the shaft, and
    the electrical connecting element is routed at an angle with respect to the longitudinal axis of the shaft at at least one location of the shaft;
    wherein the connecting element is fixed to the inner shaft tube in one or more of a proximal end of the connecting element or a distal end of the connecting element;
    the connecting element is fixed on the inner shaft tube by one or more electrically insulating heat-shrink tubings;

the video endoscope further comprising a guide for guiding the connecting element, the guide being disposed at the at least one location;
wherein the one or more heat shrinking tubings comprise a first heat shrink tubing and a second heat shrink tubing;
the first heat shrink tubing having a distal end which fixes the distal end of the connecting element and the first heat shrink tubing having a proximal end that is overlapped by the guide; and
the second heat-shrink tubing having a proximal end which fixes the proximal end of the connecting element and the second heat shrink tubing having a distal end that overlaps the guide.

* * * * *